US012654930B2

(12) United States Patent　　　(10) Patent No.:　US 12,654,930 B2
Loh　　　　　　　　　　　　　　　　　(45) Date of Patent:　Jun. 16, 2026

(54) SELF-CLEANING SECTIONAL PANEL TANK

(71) Applicant: POLY-LINE PTE LTD, Singapore (SG)

(72) Inventor: Chin Kiat Loh, Singapore (SG)

(73) Assignee: POLY-LINE PTE LTD, Singapore (SG)

( * ) Notice: Subject to any disclaimer, the term of this patent is extended or adjusted under 35 U.S.C. 154(b) by 58 days.

(21) Appl. No.: 18/433,463

(22) Filed: Feb. 6, 2024

(65) Prior Publication Data

US 2024/0174437 A1　　May 30, 2024

Related U.S. Application Data

(63) Continuation-in-part of application No. 17/599,572, filed as application No. PCT/SG2020/050677 on Nov. 20, 2020, now Pat. No. 11,926,471.

(30) Foreign Application Priority Data

Nov. 21, 2019　　(SG) ............................ 10201910976U
Dec. 26, 2019　　(MY) ............................ PI2019007789
(Continued)

(51) Int. Cl.
　　*B65D 90/00*　　　　(2006.01)
　　*A61L 2/22*　　　　(2006.01)
　　(Continued)

(52) U.S. Cl.
　　CPC ............ *B65D 90/0093* (2013.01); *A61L 2/22*
　　(2013.01); *B65D 90/023* (2013.01); *B65D*
　　　　　　　　　　　　　　　　　　*90/08* (2013.01);
　　(Continued)

(58) Field of Classification Search
　　CPC .......... A61L 2/22; A61L 2/18; A61L 2202/14;
　　　　　　　　　　　A61L 2202/15; A61L 2103/23;
　　(Continued)

(56) References Cited

U.S. PATENT DOCUMENTS 1,427,166 A　　8/1922　Parton
1,943,191 A　　1/1934　Schwemlein
(Continued)

FOREIGN PATENT DOCUMENTS

CN　　105691967 A　*　6/2016　......... B65D 90/0093
DE　　　1481070 A1　　2/1969
(Continued)

*Primary Examiner* — Benjamin L Osterhout
(74) *Attorney, Agent, or Firm* — IDEA Intellectual Limited; Sam T. Yip

(57)　　　　　　　　ABSTRACT

According to a first aspect of the present application, a self-cleaning sectional panel tank is provided. The tank comprises at least one side wall for joining other side walls in forming the sectional panel tank. The at least one side wall comprises: a first unit panel having a first extension at its edge for supporting the first unit panel; and a second unit panel having a second extension at its edge. The first unit panel and the second unit panel are joined together contiguously at the first extension and the second extension by at least one fastener; and at least one directional sprinkler nozzle connected to the at least one side wall configured to discharge a cleaning and/or disinfectant solution onto interior surfaces of the self-cleaning sectional panel tank.

20 Claims, 2 Drawing Sheets

(30) Foreign Application Priority Data

| Dec. 31, 2019 | (CN) | ........................ | 201911414932.X |
| Dec. 31, 2019 | (CN) | ........................ | 201922481683.8 |
| Jan. 30, 2020 | (KR) | ........................ | 10-2020-0011070 |

(51) Int. Cl.

| B65D 90/02 | (2019.01) |
| B65D 90/08 | (2006.01) |
| A61L 2/18 | (2006.01) |
| A61L 103/00 | (2026.01) |

(52) U.S. Cl.

CPC ............. *A61L 2/18* (2013.01); *A61L 2103/23* (2026.01); *A61L 2202/14* (2013.01); *A61L 2202/15* (2013.01)

(58) Field of Classification Search

CPC ... A61L 2202/23; B65D 90/08; B65D 90/023; B65D 90/0093

See application file for complete search history.

(56) References Cited

U.S. PATENT DOCUMENTS

| 3,410,441 | A | 11/1968 | Rhyne |
| RE27,330 | E | 4/1972 | Marcmann |
| 4,188,759 | A | 2/1980 | Liet et al. |
| 4,244,486 | A | 1/1981 | Ewald, Jr. |
| 4,376,360 | A | 3/1983 | Hanson |
| 5,052,569 | A | 10/1991 | Cooper |
| 5,449,081 | A | 9/1995 | Sjostedt et al. |
| 5,522,522 | A | 6/1996 | Fukumoto |
| 5,688,086 | A | 11/1997 | Menzemer et al. |
| 5,741,042 | A | 4/1998 | Livingston et al. |
| 6,244,063 | B1 | 6/2001 | Yates |
| 7,658,198 | B2 * | 2/2010 | Brinker ..................... B08B 9/08 |
| | | | 15/302 |
| 9,205,471 | B2 * | 12/2015 | Ross ..................... B08B 9/0936 |
| 9,314,805 | B2 * | 4/2016 | Ross ..................... B05B 15/555 |
| 9,555,959 | B1 | 1/2017 | Ziegs |
| 9,925,573 | B2 * | 3/2018 | Harman ................. B08B 9/093 |
| 2004/0107823 | A1 | 6/2004 | Kiley et al. |
| 2005/0229501 | A1 | 10/2005 | Grossman et al. |

FOREIGN PATENT DOCUMENTS

| DE | 2321953 | A1 | 11/1974 | | |
| EP | 0226776 | A2 | 7/1987 | | |
| GB | 2000216 | A | 1/1979 | | |
| JP | 2001130692 | A | 5/2001 | | |
| KR | 20080043185 | A | 5/2008 | | |
| KR | 20130066056 | A | 6/2013 | | |
| KR | 101706038 | B1 | 2/2017 | | |
| KR | 101732484 | B1 | 5/2017 | | |
| WO | 2004056677 | A1 | 7/2004 | | |
| WO | WO-2011097943 | A1 * | 8/2011 | ............... | A61L 2/18 |
| WO | 2019178688 | A1 | 9/2019 | | |
| WO | WO-2024197353 | A1 * | 10/2024 | ........... | B01D 21/302 |

* cited by examiner

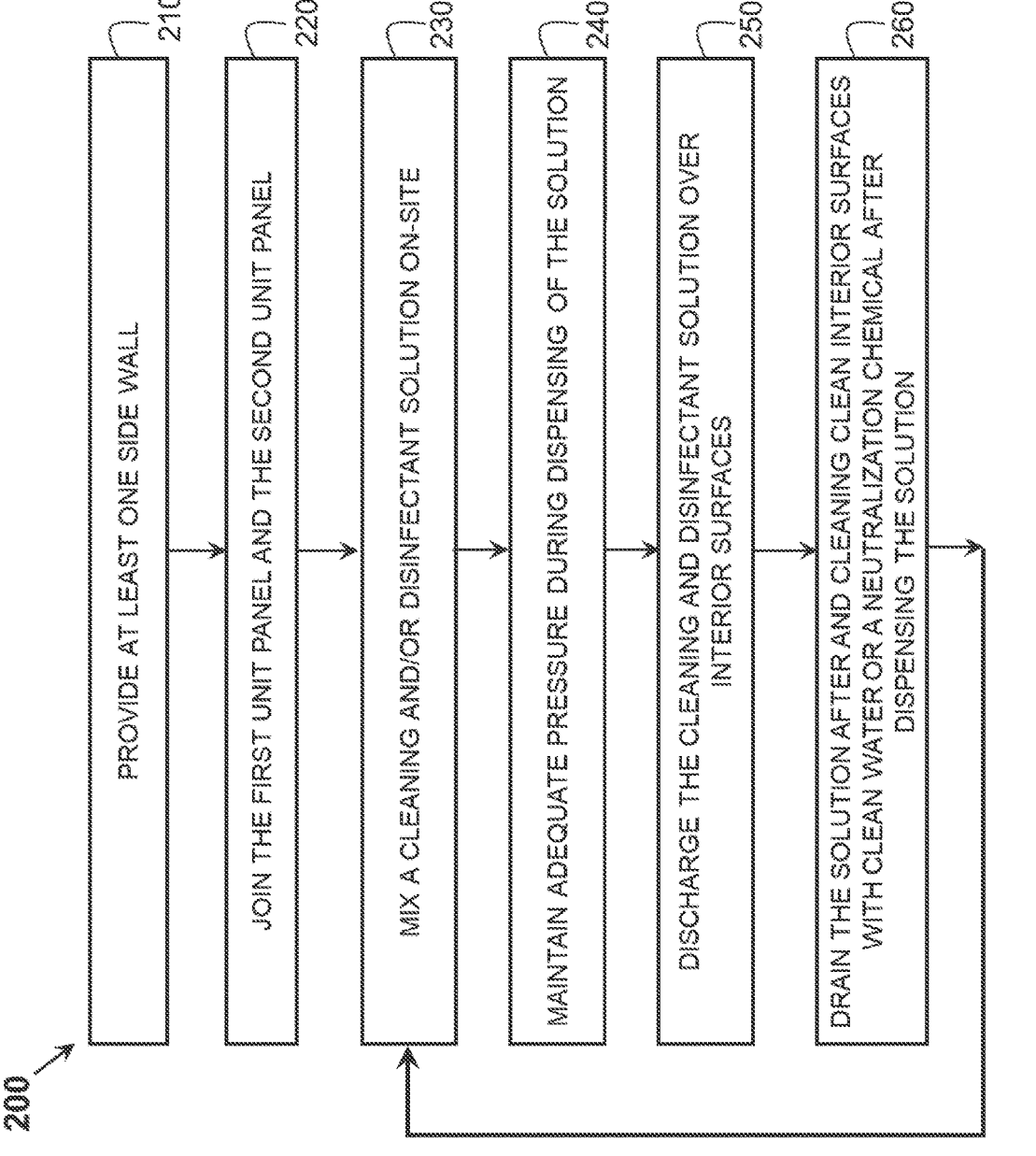

PROVIDE AT LEAST ONE SIDE WALL — 210

JOIN THE FIRST UNIT PANEL AND THE SECOND UNIT PANEL — 220

MIX A CLEANING AND/OR DISINFECTANT SOLUTION ON-SITE — 230

MAINTAIN ADEQUATE PRESSURE DURING DISPENSING OF THE SOLUTION — 240

DISCHARGE THE CLEANING AND DISINFECTANT SOLUTION OVER INTERIOR SURFACES — 250

DRAIN THE SOLUTION AFTER AND CLEANING CLEAN INTERIOR SURFACES WITH CLEAN WATER OR A NEUTRALIZATION CHEMICAL AFTER DISPENSING THE SOLUTION — 260

SELF-CLEANING SECTIONAL PANEL TANK

CROSS-REFERENCE TO RELATED APPLICATIONS

The present application is a continuation-in-part of the U.S. non-provisional patent application Ser. No. 17/599,572 filed Sep. 29, 2021, which claims priority from (i) Korean invention patent application no. 10-2020-0011070 filed Jan. 30, 2020, (ii) Chinese utility model patent application no. 201922481683.8 filed Dec. 31, 2019, (iii) Chinese invention patent application no. 201911414932.X filed Dec. 31, 2019, (iv) Malaysian patent application no. PI2019007789 filed Dec. 26, 2019, and (v) Singaporean patent application no. 10201910976U filed Nov. 21, 2019, and the disclosures of which are incorporated by reference in their entirety.

FIELD OF THE INVENTION

The field of this invention pertains to liquid storage systems, specifically to the design and operation of sectional panel tanks used for storing water and other liquids. It relates to the mechanisms and methods for maintaining the cleanliness and hygiene of such tanks through automated self-cleaning processes that employ integrated sprinkler systems for the distribution of cleaning and disinfectant solutions. This invention falls within the technical field of industrial cleaning systems, with a particular focus on improving maintenance efficiency and ensuring compliance with health and safety standards in water storage facilities.

BACKGROUND

Traditional cleaning methods typically require manual labour to scrub and rinse the tank's interior surfaces. This process is labour-intensive, time-consuming, and can lead to inconsistent cleaning results. Manual cleaning necessitates significant downtime for the tank, interrupting regular operations and leading to potential losses, especially in industrial or municipal settings where continuous water supply is critical. Some tanks have hard-to-reach areas, making thorough cleaning difficult. This can result in the accumulation of sediments, biofilms, and other contaminants that can compromise the quality of the stored liquid. Personnel performing manual cleaning may be exposed to hazardous conditions, especially when dealing with chemicals or confined spaces that pose health risks. The handling and dosing of cleaning chemicals require precision and can pose environmental and safety risks if not managed properly. Ensuring that tanks meet health and safety regulations through manual cleaning can be challenging, leading to potential violations and associated penalties.

Therefore, there is a need in the art for a self-cleaning sectional panel tank which can overcome these drawbacks. The present invention addresses these drawbacks by introducing an automated self-cleaning tank system.

The present application is described hereinafter by various embodiments. This application may, however, be embodied in many different forms and should not be construed as limited to the embodiment set forth herein.

The principle behind the invention of the self-cleaning sectional panel tank is to automate the cleaning process of tank interiors, ensuring effective and consistent hygiene maintenance with minimal manual intervention. The tank is designed to incorporate unit panels that join together to form the tank's structure, and include strategically placed directional sprinkler nozzles that dispense a cleaning and/or disinfectant solution throughout the interior surfaces. The primary problem statement addressed by this invention is the challenge of maintaining cleanliness and hygiene in sectional panel tanks, which are commonly used for storing water and other liquids.

Traditional cleaning methods are labour-intensive, time-consuming, and often insufficient, leading to contamination risks and difficulty in complying with health and safety regulations. This invention aims to solve these problems by providing a self-cleaning tank that can automatically mix and dispense cleaning solutions, effectively reach all interior surfaces with adjustable nozzles, and monitor and maintain water quality through integrated sensors and automation technologies. The system is designed to be self-contained, reducing the need for external cleaning services, and to ensure that the tank can be kept clean with minimal downtime and operational disruption.

SUMMARY OF THE INVENTION

According to a first aspect of the present application, there is provided a self-cleaning sectional panel tank. The tank comprises at least one side wall for joining other side walls in forming the sectional panel tank. The at least one side wall comprises a first unit panel having a first extension at its edge for supporting the first unit panel; and a second unit panel having a second extension at its edge. The first unit panel and the second unit panel are joined together contiguously at the first extension and the second extension by at least one fastener; and at least one directional sprinkler nozzle connected to the at least one side wall configured to discharge a cleaning and/or disinfectant solution onto interior surfaces of the self-cleaning sectional panel tank. Alternatively, instead of fixed directional sprinkler nozzles, the tank could utilize a network of retractable nozzles that extend during the cleaning cycle and retract when not in use to protect them from damage and reduce the risk of interference with the tank's contents. These nozzles could be embedded within the panel walls themselves and connected to an internal manifold that distributes the cleaning and/or disinfectant solution evenly throughout the tank.

In accordance with an embodiment of the present invention, the tank includes an external water pump connected to the sprinkler nozzle to maintain adequate pressure for the cleaning solution. Another embodiment may use an internal pump system that is built into the tank's structure to conserve space.

In accordance with an embodiment of the present invention, the cleaning solution is mixed on-site before the cleaning process. An embodiment could include a pre-mixed solution that is activated by a catalyst introduced just before the cleaning process.

In accordance with an embodiment of the present invention, the solution is drained from the tank after cleaning. An alternative embodiment could use a filtration and recycling system to reduce waste.

In accordance with an embodiment of the present invention, the tank's interior is rinsed with clean water or a neutralization chemical after dispensing the solution. Another embodiment could involve a drying phase using air circulation to remove excess moisture.

In accordance with an embodiment of the present invention, the nozzles can rotate to aerosolize the solution within the tank. An embodiment could feature stationary nozzles combined with a pressurized system to ensure coverage.

In accordance with an embodiment of the present invention, a mixing station automates the dispensing of the solution and clean water using dosing pumps and valves, controlled via Internet of Things automation (IoTA). A manual version of the mixing station could be used in settings where digital automation is not feasible.

In accordance with an embodiment of the present invention, the tank is equipped with inline sensors for water quality monitoring post-cleaning. An embodiment could have periodic manual sampling for water quality assessment.

In accordance with an embodiment of the present invention, the IoTA-configured inline sensors inform authorities of compliance with water quality standards. Alternatively, a system could involve manual reporting to authorities based on scheduled tests.

In accordance with an embodiment of the present invention, the tank features both fixed and rotatable sprinkler heads for comprehensive interior coverage. Another embodiment could include modular nozzle heads that can be manually adjusted or replaced as needed for different coverage patterns In accordance with an embodiment of the present invention, the sprinkler nozzles are strategically placed for uniform distribution of the cleaning solution. In an alternative embodiment, the nozzles could be designed to move along tracks for adjustable positioning.

In accordance with an embodiment of the present invention, sensors integrated within the tank detect water levels to initiate cleaning automatically. Another embodiment might use a manual initiation system that begins the cleaning process based on user input.

In accordance with an embodiment of the present invention, the external water pump is equipped with variable speed control to adjust the cleaning solution's flow rate. An embodiment could feature pumps with pre-set speeds for different tank sizes, eliminating the need for variable control.

In accordance with an embodiment of the present invention, a booster pump ensures effective reach and dispersion of the cleaning solution. Alternatively, the system could be designed for passive dispersion that relies on the natural flow of water.

In accordance with an embodiment of the present invention, check valves are integrated to prevent backflow and maintain directional flow of the solution. An embodiment could use mechanical barriers or siphon breaks instead of check valves to prevent backflow.

In accordance with an embodiment of the present invention, the mixing station is capable of preparing multiple types of cleaning solutions. A simpler embodiment might employ a single, universal cleaning solution to streamline the cleaning process.

In accordance with an embodiment of the present invention, multiple dosing pumps allow for precise metering of various chemicals into the solution. An embodiment could use gravity-fed dosing to simplify the chemical metering process.

In accordance with an embodiment of the present invention, motorized valves controlled by IoTA automate the regulation of water and cleaning chemicals into the mixing station. A manual valve system could be used for environments where automation is not practical.

In accordance with an embodiment of the present invention, the dosing pumps handle various types of cleaning chemicals, including alkaline, acidic, and neutral agents. An embodiment might feature a single pump system with a selector for different types of chemicals.

According to a second embodiment of the present invention, there is provided a method for a self-cleaning a sectional panel tank. The method comprises steps of providing at least one side wall, wherein the at least one side wall comprises a first unit panel with a first extension at its edge and a second unit panel with a second extension at its edge; joining the first unit panel and the second unit panel together contiguously at the first extension and the second extension using at least one fastener; mixing the cleaning and/or disinfectant solution on-site before each cleaning; discharging a cleaning and disinfectant solution over interior surfaces of the tank using one or more directional sprinkler nozzles; maintaining adequate pressure during dispensing of the solution using an external water pump connected to the sprinkler nozzles; draining the solution after cleaning; and cleaning interior surfaces with clean water or a neutralization chemical after dispensing the solution. An alternative method for self-cleaning a sectional panel tank could involve a the side walls that would interlock, reducing the need for fasteners. The cleaning solution could be preformulated and activated by a trigger rather than being mixed on-site. Finally, the interior surfaces could be treated with an advanced hydrophobic coating that repels contaminants, reducing the frequency and intensity of cleaning required.

In accordance with an embodiment of the present invention, the method includes rotating the nozzles to aerosolize the solution throughout the tank. An embodiment could use a pulsating nozzle system to distribute the cleaning solution without rotation.

In accordance with an embodiment of the present invention, the dispensing of the solution and clean water is automated using IoTA-configured dosing pumps and valves. A semi-automated system requiring partial manual operation could be used in certain applications.

In accordance with an embodiment of the present invention, the method incorporates the integration of inline sensors for water quality monitoring and statutory compliance notification via IoTA. An alternative could include a manual checklist and records for compliance purposes.

In accordance with an embodiment of the present invention, the method activates both fixed and rotatable sprinkler heads for complete tank coverage. An embodiment might use a combination of fixed heads and manually rotated nozzles for selective coverage.

In accordance with an embodiment of the present invention, water pressure is increased using a booster pump to enhance the effectiveness of the cleaning process. The system could be configured to operate at a standard water pressure, using more effective nozzles to compensate.

In accordance with an embodiment of the present invention, the method includes preventing backflow using check valves. An embodiment might position the tank such that gravity assists in preventing backflow without the need for valves.

In accordance with an embodiment of the present invention, the method involves using multiple dosing pumps to introduce different cleaning chemicals. A single dosing system with a manually changeable input could be used for different chemicals.

In accordance with an embodiment of the present invention, the flow regulation of water and chemicals is automated via motorized valves and IoTA. An embodiment could involve manual adjustments to the flow based on observed cleaning efficacy.

In accordance with an embodiment of the present invention, the method allows for user control through an interface connected to the IoTA, providing manual adjustments to the cleaning cycles. A basic embodiment could feature pre-set cleaning cycles that do not require user input.

In accordance with an embodiment of the present invention, the method includes selecting and dosing different types of cleaning chemicals with the dosing pumps to address specific contaminants. An embodiment could use a set mixture of chemicals in a fixed ratio for a generalized cleaning process.

In accordance with an embodiment of the present invention, the method includes the on-site preparation of a fresh batch of cleaning and/or disinfectant solution. Once this new solution is mixed, it is used for a further cleaning process within the tank. The method implies a multi-stage cleaning method, where the tank may undergo multiple cleaning cycles with freshly prepared solutions for improved cleaning efficacy.

Embodiments of relevant invention(s) provide a self-cleaning sectional panel tank that the cleaning and disinfectant solution are preferably mixed on-site before cleaning process. Additionally, the cleaning and/or disinfectant solution may be drained from the tank after cleaning. Optionally, the inline sensors, using IoTA, are configured to inform relevant authorities of fulfilment of statutory requirements for maintaining potable water tanks. Preferably, multiple directional sprinkler nozzles are positioned at strategically determined locations on the side walls to ensure uniform distribution of the cleaning and/or disinfectant solution over the interior surfaces. The self-cleaning sectional panel tank can further comprise at least one (i.e., one or more) sensor integrated within the side walls to detect a level of water and initiate cleaning process automatically when the tank is vacant or at a defined low water level. The external water pump is preferably equipped with variable speed control to adjust a pressure and flow rate of the cleaning and/or disinfectant solution based on size and configuration of the tank. Multiple dosing pumps are sometimes provided to the self-cleaning sectional panel tank for precise metering of various chemicals into the solution, where individual pumps are connected to a separate chemical supply line. Occasionally, the dosing pumps are configured to handle different types of cleaning chemicals, selected from alkaline, acidic, and neutral agents, to match the cleaning requirements of various contaminants Embodiments of relevant invention(s) further provide a method for self-cleaning a sectional panel tank, which additionally comprises the step of preventing backflow of the cleaning and/or disinfectant solution using check valves integrated into supply lines connected with the external pump. The method for self-cleaning a sectional panel tank preferably further comprises the step of providing user control through an interface connected to the IoTA, allowing manual adjustments to cleaning cycles, including the composition and volume of the cleaning and/or disinfectant solution. The method for self-cleaning a sectional panel tank optionally further includes the step of selecting and dosing different types of cleaning chemicals, selected from a group comprising alkaline, acidic, or neutral agents, with the dosing pumps to address specific contaminants.

BRIEF DESCRIPTION OF THE DRAWINGS

The accompanying Figures (i.e., FIGS. or FIGS) illustrate embodiments and serve to explain principles of the disclosed embodiments. It is to be understood, however, that these Figures are presented for purposes of illustration only, and not for defining limits of relevant applications. It is to be noted, however, that the appended drawings illustrate only typical embodiments of this application and are therefore not to be considered limiting of its scope, for the application may admit to other equally effective embodiments.

These and other features, benefits, and advantages of the present application will become apparent by reference to the following text Figure, with like reference numbers referring to like structures across the views, wherein:

FIG. 2 illustrates a method of working of the self-cleaning sectional panel tank, in accordance with an embodiment of the present application.

DETAILED DESCRIPTION

Figure 1:
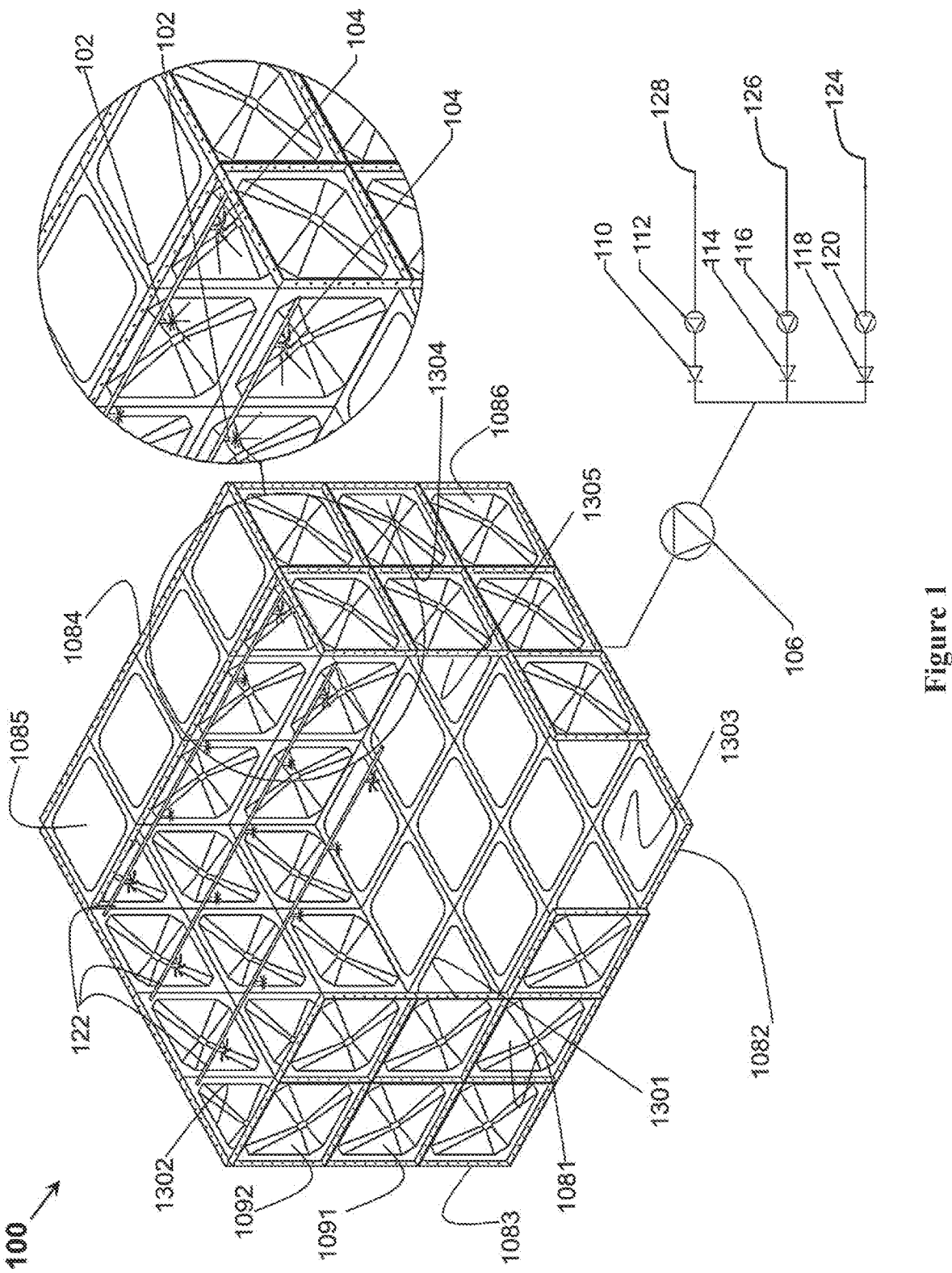
FIG. 1 illustrates a self-cleaning sectional panel tank, in accordance with an embodiment of the present application.

The present application is described hereinafter by various embodiments with reference to the accompanying drawing, wherein reference numerals used in the accompanying drawing correspond to the like elements throughout the description. While the present application is described herein by way of example using embodiments and illustrative drawings, those skilled in the art will recognize that the application is not limited to the embodiments of drawing or drawings described and are not intended to represent the scale of the various components. Further, some components that may form a part of the application may not be illustrated in certain Figures, for case of illustration, and such omissions do not limit the embodiments outlined in any way. It should be understood that the drawings and detailed description thereto are not intended to limit the application to the particular form disclosed, but on the contrary, the application is to cover all modifications, equivalents, and alternatives falling within the scope of the present application as defined by the appended claim. As used throughout this description, the word "may" is used in a permissive sense (i.e., meaning having the potential to), rather than the mandatory sense, (i.e., meaning must). Further, the words "a" or "an" mean "at least one" and the word "plurality" means "one or more" unless otherwise mentioned. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes.

FIG. 1 illustrates a self-cleaning sectional panel tank 100, in accordance with an embodiment of the present application. As shown in FIG. 1, the self-cleaning sectional panel tank 100 comprises side wall, first unit panel 1091, second unit panel 1092, one directional sprinkler nozzles 102, 104, an external water pump 106, check valves 110, 114, 118, motorized valves 112, and dosing pumps 116, 120.

A first side wall 1081, a second side wall 1082, a third side wall 1083, a fourth side wall 1084, a fifth side wall 1085, and a sixth side wall 1086 (hereinafter, collectively called "the side walls 1081, 1082, 1083, 1084, 1085, 1086") are constructed from multiple unit panels 1091, 1092 that join together to form the tank 100. Each unit panel has extensions at its edges. The side walls 1081, 1082, 1083, 1084, 1085, 1086 are fundamental structural components of the tank 100. They are assembled to create the tank's 100 periphery.

Comprised of multiple unit panels 1091, 1092, these walls serve as the primary containment structure, keeping the stored water within and providing the surface against which cleaning solutions are sprayed.

There are first and second unit panels 1091, 1092, each with extensions at their edges for support and connectivity. The tank 100 is modular in design, with each side wall 1081 constructed from a series of unit panels 1091, 1092. These unit panels 1091, 1092 are individual sections that fit together to form a complete wall. Each unit panel features or includes an extension at its edges, which are protrusions or flanges designed to overlap or fit snugly with adjacent panels. The first unit panel 1091 refers to one of the two primary types of panels used to construct a side wall, and the second unit panel 1092 is the complementary type that joins with the first to complete the wall structure.

Fasteners are used to contiguously join the unit panels 1091, 1092 at their respective extensions. Fasteners are mechanical securing devices, such as bolts, screws, or rivets, which are used to join the first and second unit panels 1091, 1092 at their extensions. They ensure a contiguous, secure fit between panels, maintaining the tank's 100 structural integrity and preventing leaks. The fasteners are designed to withstand the stress of filled water and the chemical exposure during cleaning. In accordance with an embodiment of the present invention, gaskets may be disposed between the unit panels 1091, 1092 as sealant. The gaskets serve as a sealing layer between the panels, enhancing the leak-proof quality of the tank. They fill any small gaps or irregularities between the panel surfaces, preventing water from seeping through the joints. The material of the gasket is usually resilient and chemically resistant, ensuring it can withstand the environmental conditions inside the tank 100, including exposure to water and cleaning chemicals. The gaskets also help to absorb any mechanical stress or minor movements between the panels 1091, 1092, thus reducing the risk of leaks over time.

Further, attached to the interior of the side walls 1081, 1082, 1083, 1084, 1085, 1086, the directional sprinkler nozzles 102, 104 are key to the self-cleaning functionality. At least one nozzle is connected to a side wall 1081 and configured to spray a cleaning/disinfectant solution onto the tank's 100 first interior surface 1301, second interior surface 1302, third interior surface 1303, fourth interior surface 1304, and fifth interior surface 1305 (hereinafter collectively called "interior surfaces 1301, 1302, 1303, 1304, 1305"). These nozzles 102, 104 can be aimed or adjusted to direct the flow of cleaning/disinfectant solution to specific areas within the tank 100. They are capable of covering the interior surfaces 1301, 1302, 1303, 1304, 1305 of the tank 100, ensuring that the cleaning solution reaches all areas for effective cleaning. The term "directional" implies that the spray pattern or direction can be controlled, either manually or automatically, to optimize the cleaning process.

In accordance win an embodiment of the present invention, the nozzles 102, 104 may rotate to cover the entire interior of the tank 100. Rotatable nozzles 104 are a type of directional sprinkler nozzle that can pivot or rotate to direct the cleaning solution to different parts of the tank 100. These nozzles 102, 104 can be programmed or manually adjusted to ensure complete coverage, especially in corners or under surfaces that fixed nozzles 102 might miss. The rotation allows for a dynamic cleaning process that can adapt to the tank's 100 geometry and any obstructions within.

In an embodiment of the present invention, the nozzle may include both fixed nozzles 102 for steady streams and rotatable nozzles 104 for comprehensive coverage. The tank

100 employs two types of sprinkler nozzles 102, 104. The fixed nozzle 102 deliver a consistent and steady stream of cleaning solution to designated areas. The rotatable nozzles 104 can pivot or spin, providing dynamic coverage and the ability to reach variable angles and surfaces within the tank 100 that may otherwise be missed by fixed nozzles 102. The combination of fixed and rotatable nozzles 104 ensures that the entire interior of the tank 100 can be thoroughly cleaned, with the rotatable nozzles 104 complementing the fixed nozzles 102 by covering gaps in the spray pattern.

The nozzles 102, 104 may be located to uniformly distribute the solution over the tank's 100 interior. The placement of the nozzles 102, 104 is carefully considered to maximize the effectiveness of the cleaning process. Nozzles 102, 104 are positioned at locations that allow for even distribution of the cleaning solution across all interior surfaces 1301, 1302, 1303, 1304, 1305 of the tank 100, including corners and edges. Strategic positioning helps avoid shadowed areas where the spray might not normally reach, ensuring a more uniform distribution and thorough cleaning process.

The self-cleaning sectional panel tank 100 may comprise external water pump 106 connected to the sprinkler nozzles 102, 104 to maintain pressure for dispensing the solution. As shown in FIG. 1, at least one conduit 122 may inter connect series of the sprinkle nozzles 102, 104. As shown in FIG. 1, there may be multiple conduits disposed within the tank 100 connecting the nozzles 102, 114. As shown in FIG. 1, there may be multiple conduits disposed within the tank 100 connecting various nozzles 102, 114 inside the tank 100. The pump 106 may be installed outside of the tank 100 and is part of the plumbing system that supplies the cleaning and/or disinfectant solution to the sprinkler nozzles 102, 104. Its primary function is to ensure that the solution is dispensed under adequate pressure, which is necessary for the nozzles 102, 104 to effectively distribute the cleaning agents over the tank's 100 interior surfaces 1301, 1302, 1303, 1304, 1305. The pump 106 may vary in capacity and power depending on the size of the tank 100 and the required pressure to achieve optimal cleaning coverage.

In accordance with an embodiment of the present invention, the external pump 106 may be a variable speed water pump 106 that can adjust flow rate and pressure based on the tank's 100 requirements. The external pump 106 is designed with the capability to vary its speed, which in turn allows for control over the flow rate and pressure of the water and cleaning solution. By adjusting the speed, the pump 106 can adapt to the cleaning requirements based on the tank 100 size, the type of cleaning agents being used, and the desired intensity of the cleaning process. This feature adds flexibility and efficiency to the cleaning process, conserving energy when full power is not needed and providing extra pressure when heavy cleaning is required.

In accordance with an embodiment of the present invention, the external pump 106 may be a booster pump 106, a specific type of external pump used to increase water pressure. The booster pump 106 is a dedicated device that increases the pressure of the water being delivered to the sprinkler nozzles 102, 104. It is typically used when the existing pressure is insufficient to achieve the desired flow rate for the sprinklers to effectively cover the tank's 100 interior surfaces 1301, 1302, 1303, 1304, 1305. This pump 106 can be particularly useful in larger tanks or in situations where the water supply has a naturally low pressure.

In additional, the self-cleaning sectional panel tank 100 may include multiple dosing pumps 116, 120 for precise metering of different chemicals into the solution, each connected to a unique chemical line. The dosing pumps 116, 120 can accurately meter out various types of cleaning agents, such as alkaline solutions for greasy residues, acidic solutions for mineral deposits, and neutral chemicals for general cleaning purposes. The versatility also allows for the use of specific disinfectants to target certain types of bacteria or viruses, ensuring the tank 100 can be adapted to meet different sanitation standards. The dosing pumps 116, 120 may be used to inject precise amounts of chemicals into the water to create the cleaning solution. Having multiple dosing pumps 116, 120 enables the tank 100 to meter out multiple cleaning chemicals simultaneously or sequentially, depending on the desired cleaning solution composition. Each pump is typically connected to its own separate chemical supply line and can be individually controlled to achieve the correct dosage.

As shown in the FIG. 1, a first supply line 124 may be connected with a first dosing pump 120. The first supply line 124 may supply a chemical A meant for forming the solution for cleaning. Similarly, as shown in FIG. 1, a second supply sine 126 may be connected with a second dosing pump 116. The second supply line 126 may supply a chemical B meant for forming the solution for cleaning.

In accordance with an additional or alternative embodiment, a mixing station may be equipped with dosing pumps 116, 120 and actuated valves, automated via Internet of Things (IOT) technology. The mixing station may be a dedicated component that automates the preparation of the cleaning solution. Equipped with dosing pumps 116, 120, it can precisely meter the required amounts of various chemicals into the mix. Actuated valves, controlled by IoT technology, can regulate the flow of chemicals and water, mixing them as needed. The automation provided by IoT allows for remote monitoring and control, as well as integration with other systems for a more intelligent cleaning process.

The solution is prepared within the tank 100 before the cleaning process. Refers to the capability of the tank 100 to prepare the cleaning and disinfectant solutions on the premises, just before the commencement of the cleaning cycle. This ensures that the chemical agents are fresh and at the correct concentration, which can be crucial for effective cleaning and to maintain the quality standards of the stored water. It also allows for the flexibility of adjusting the cleaning solution composition based on specific cleaning requirements or water quality conditions.

In an embodiment of the present invention, the self-cleaning sectional panel tank 100 may include a multi-solution mixing station capable of preparing various types of cleaning solutions. A mixing station designed to handle various types of cleaning solutions, which can be selected based on the specific cleaning needs of the tank 100. It allows for the use of different cleaning agents-such as those targeting mineral deposits, biological growth, or other contaminants by mixing them in the correct proportions. This station may include storage for multiple chemicals and the ability to switch between them as needed.

In accordance with an additional or alternative embodiment of the present invention, the mixing station and/or the external water pump 106 are mobile and portable and are connected with the sprinkler nozzles 102, 104 when the need arises. The mixing station and/or the external water pump 106 may include features such as wheels or a compact, lightweight construction that facilitates transportation. These units may also have handles, towing mechanisms, or be mountable on a vehicle or a cart for ease of movement. The portability is particularly useful for situations where the tank 100 is located in a remote area, or where a permanent installation of cleaning equipment is impractical.

The mixing station can either be installed onsite, or as a mobile unit for those that don't require any chemicals onsite or those that don't have sufficient space to accommodate a mixing station permanently. A mobile unit may be connected to pre-installed sprinkler heads and pipe works to deploy for cleaning, disinfection, neutralization, etc.

Further, the inline sensors may be integrated within the supply lines to monitor water quality post-cleaning. These sensors such as, but not limited to, pH sensors, residual disinfectant sensors, turbidity sensors, microbial presence sensors, conductivity sensors, that are installed within the tank's 100 supply lines 128, 126, 124, designed to activate and take readings as needed, particularly after the cleaning process. Their primary role is to assess the quality of the water by checking for parameters such as PH levels, residual disinfectant concentrations, turbidity, and possibly microbial presence. They ensure that the water quality remains within acceptable limits and that the cleaning process has not adversely affected the water intended for storage.

The inline sensors may inform relevant authorities about water quality, ensuring statutory compliance. These are the inline sensors with connectivity features that enable them to communicate data via the Internet of Things Automation (IoTA) network. The present invention incorporates an advanced Internet of Things Automation (IoTA) designed to intelligently connect and manage a network of devices, sensors, and actuators through a centralized platform. This IoTA utilizes a combination of wireless communication protocols, real-time data processing, and adaptive control algorithms to facilitate autonomous operation of the connected devices. It is equipped with robust security features to safeguard data integrity and system operations.

The innovation detailed herein is particularly suited for applications requiring precision control, energy management, resource conservation, and overall system efficacy. It represents a significant improvement over traditional automated systems by offering a dynamic and self-improving operational framework. This IoTA is essential to the operation of [insert specific application or device, e.g., 'the self-cleaning sectional panel tank 100'] as it enables the seamless coordination of [insert specific functions, e.g., 'cleaning cycles, solution mixing, and dispensing processes'] with minimal human intervention. The IoTA architecture supports a high degree of customization, allowing users to tailor the functionality to their specific requirements. The technical features and advantages of the IoTA as disclosed herein form the basis of its novelty and utility in the context of this patent document.

The data collected by the inline sensors can be automatically sent to relevant authorities or systems to report on the tank's 100 water quality, facilitating real-time monitoring and compliance with health and safety regulations. The inline sensors may monitor water quality after cleaning to detect any residual solution or deterioration in water quality. This technology ensures a proactive approach to water quality management, allowing for immediate action if the water quality deteriorates or if the cleaning process leaves behind residues that could affect potability.

In an additional or alternative embodiment of the present invention, the self-cleaning sectional panel tank 100 may include one or more check valves 110, 114, 118 configured to prevent backflow in the supply lines and ensure directional flow of the solution. The check valves 110, 114, 118 are one-way valves that only allow the solution to flow in one direction. They are critical safety features that prevent the cleaning solution from flowing backwards into the clean water supply or other parts of the tank 100 where it should not go. These valves are essential for maintaining the purity of the water supply and for the correct operation of the cleaning process. As shown in FIG. 1, the check valves 110, 114, 118 are disposed corresponding to the supply lines 128, 126, 124. As shown in FIG. 1, the first check valve 118 is disposed corresponding to the first supply line 124 and the first dosing pump 120, where the first supply line 124 may be providing chemical A. similarly, the second check valve 114 is disposed corresponding to the second supply line 126 and the second dosing pump 116, where the second supply line 126 may be providing chemical B. The third supply line 128 is for potable water, connected with the third check valve 110.

Further, the self-cleaning sectional panel tank 100 may include motorized valve 112 controlled by IoT technology for automated flow regulation. These are valves operated by motors rather than manually, and their operation can be controlled remotely through IoT technology. The motorized valve 112 can be programmed to open or close to regulate the flow of water and/or chemicals into the mixing station, as part of the automated cleaning process. They allow for fine-tuned control over the mixing of cleaning solutions, as well as the ability to quickly shut off the flow in case of a problem. As shown in the FIG. 1, a third supply line 128 adapted to supply potable water to the motorized valves 112. The potable water is then mixed with the chemical A and B used for formation of the cleaning solution.

In an additional or alternative embodiment of the present invention, the self-cleaning sectional panel tank 100 may include solution drainage configured to drain the solution from the tank 100 after cleaning. After the cleaning cycle is completed, the used solution containing dirt, debris, and potentially hazardous chemicals needs to be removed from the tank 100. This may be done via a drainage system designed to safely and efficiently evacuate the spent solution from the tank 100 to prevent contamination of the stored water and to prepare the tank 100 for its next use. The drainage system typically includes outlets, valves, and possibly a treatment or neutralization step before the solution is disposed of or recycled.

Further, in accordance with an embodiment of the present invention, the interior surfaces 1301, 1302, 1303, 1304, 1305 are cleaned with either clean water or a neutralization chemical after the disinfectant is dispensed. Following the application of the disinfectant solution, the tank's 100 interior surfaces 1301, 1302, 1303, 1304, 1305 may require additional cleaning with clean water or a chemical that neutralizes the disinfectant. It is crucial to ensure that no harmful residues remain that could affect the water quality or safety. The process involves rinsing or applying another cleaning agent to neutralize and remove any remaining disinfectant.

Further, in an additional or alternative embodiment of the present invention, the self-cleaning sectional panel tank 100 may include water level sensors such as, but not limited to, float-type level sensors, ultrasonic level sensors, capacitive level sensors, optical water level sensors, conductive level sensors, radar level sensors integrated to detect water levels and initiate cleaning as needed. This self-cleaning sectional panel tank 100 includes sensors that detect the current water level inside the tank 100. It can automatically trigger the initiation of the cleaning process when the water level falls below a certain threshold, ensuring that cleaning occurs when the tank 100 is empty or low (nearly empty). This system prevents the unnecessary dilution of cleaning solutions and ensures that cleaning does not interfere with the tank's 100 primary function of water storage.

Additionally, the self-cleaning sectional panel tank 100 may include integrated channelling built into the side walls 1081, 1082, 1083, 1084, 1085, 1086 to house the supply lines. The integrated channelling may refer to channels or ductwork integrated into the tank's 100 walls 1081 that house the supply lines for the cleaning solution. It is designed to keep the supply lines secure and out of the way, reducing the risk of damage and maintaining the tank's 100 aesthetic and structural integrity. It also simplifies maintenance and inspection by providing an organized pathway for the lines.

Moreover, the self-cleaning sectional panel tank 100 may include filter adapted to safely dispose of the cleaning solution while protecting the environment. Once the cleaning process is complete, the used solution needs to be removed from the tank 100. The filtration may ensure that the solution is safely and efficiently directed out of the tank 100. The filter can capture any particulate matter or residues from the cleaning process, preventing them from entering the environment. The filter is essential for environmental protection and for complying with regulations regarding the discharge of cleaning chemicals.

In accordance with an additional or alternative embodiment of the present invention the self-cleaning sectional panel tank 100 may include user Interface and IoTA for manual control and customization of cleaning cycles. The User Interface (UI) serves as the point of interaction between the user and the self-cleaning tank, often featuring a display and input controls. It allows operators to manually initiate cleaning cycles, customize settings such as the timing and intensity of the cycles, and adjust the composition of the cleaning solution according to specific needs. The IoTA enhances the UI by enabling remote access and control, data collection, and monitoring. It can also provide notifications and alerts about the tank's 100 status, maintenance needs, or operation anomalies. The integration of IoTA allows for the scheduling of cleaning cycles, tracking of resource usage, and analysis of long-term performance data for optimization.

EXAMPLES

An embodiment of the invention optionally or preferably works in following manner.

FIG. 2 illustrates a method 200 of working of the self-cleaning sectional panel tank, in accordance with an embodiment of the present application.

Step 210 (Provide at least one side wall): As shown in FIG. 1, at step 210, at least one side wall 1081 is provided. The at least one side wall 1081 comprises a first unit panel 1091 with a first extension at its edge and a second unit panel 1092 with a second extension at its edge. The at least one side wall 1081 serves a dual purpose. Structurally, it contributes to the formation of the tank 100, and functionally, it supports at least one directional sprinkler nozzle. This nozzle is a critical component of the tank's 100 self-cleaning mechanism, designed to discharge a cleaning and/or disinfectant solution onto the interior surfaces 1301, 1302, 1303, 1304, 1305 of the tank 100. The side wall's 1081, 1082, 1083, 1084, 1085, 1086 design integrates the functionality of the self-cleaning sectional panel tank 100 within the structural components, enhancing the efficacy of the self-cleaning process while maintaining the tank's 100 integrity.

The first unit panel 1091 possesses a first extension at its edge. This extension is not merely a protrusion but is specifically designed to facilitate the alignment and connection with the second unit panel 1092. The nature of the first extension may be such that it contributes to the structural strength, precision of assembly, or aesthetic of the side wall 1081. Similarly, the second unit panel 1092 includes a second extension at its edge. This extension aligns with the first extension of the first unit panel 1091. Together, they form a contiguous junction, ensuring a seamless interface between the two unit panels 1091, 1092.

Step 220 (Join the first unit panel 1091 and the second unit panel 1092): as shown in FIG. 2, at step 220, joining the first unit panel 1091 and the second unit panel 1092 together contiguously at the first extension and the second extension using at least one fastener. The assembly is achieved by joining a first unit panel 1091 and a second unit panel 1092 contiguously at their respective extensions using at least one fastener. The term 'contiguously' implies that the first unit panel 1091, with a first extension at its edge, and the second unit panel 1092, with a second extension at its edge, are joined without gaps or spaces. This precise joining is critical to the integrity of the tank 100 and ensures that the interior is adequately sealed for the self-cleaning process. The panels are joined using at least one fastener. This could include a variety of fastening mechanisms, which could be screws, bolts, welding, or any other suitable fastening method that provides the required strength and stability for the side walls 1081, 1082, 1083, 1084, 1085, 1086 of the tank 100. The joining of the panels 1091, 1092 not only forms the physical structure of the tank 100 but also serves as the support for directional sprinkler nozzles 102, 104, which are integral to the self-cleaning feature of the tank 100. The design and positioning of the panels take into account the placement and operation of these nozzles 102, 104. The panels 1091, 1092 are joined together using at least one fastener, a term that encompasses a broad range of possible securing devices, which could include but is not limited to, screws, bolts, clips, or adhesives. The fastener is chosen based on requirements for strength, durability, and ease of assembly or disassembly.

Step 230 (Mix a cleaning and/or disinfectant solution on-site): as shown in FIG. 2, at step 230, mixing the cleaning and/or disinfectant solution on-site before each cleaning. FIG. 2 sets the stage for step 230, which details the preparation of the cleaning and disinfectant solution used in the self-cleaning sectional panel tank 100. The method 200 involves the on-site mixing of the solution immediately before each cleaning cycle, highlighting the ability to produce a fresh and potent cleaning agent as required. The self-cleaning a sectional panel tank 100 may select and dose different types of cleaning chemicals, such as alkaline, acidic, or neutral agents, with the dosing pumps 116, 120 to address specific contaminants.

The mixing station is utilized for the preparation of the cleaning solution. The mixing station may be designed to automate the dispensing of the solution and/or clean water using a series of dosing pumps 116, 120 and actuated valves, which may be managed by Internet of Things automation (IoTA). This ensures precision and consistency in the solution's composition. The solution is composed of multiple chemical components, which are metered and introduced into the mixing station using a plurality of dosing pumps 116, 120. Each pump 116, 120 is connected to a separate chemical supply line, allowing for a customizable solution based on the tank's 100 specific cleaning requirements. The motorized valves 112 in the supply lines, controlled by IoTA, regulate the flow of potable water and/or cleaning chemicals into the mixing station. The IoTA allows for adjustments to be made in real-time, adapting to the needs of each cleaning cycle.

In accordance with an embodiment of the present invention, the self-cleaning a sectional panel tank 100 may provide user control through an interface connected to the IoTA, allowing manual adjustments to the cleaning cycles, including the composition and volume of the cleaning solution.

The self-cleaning sectional panel tank 100 may be capable of preparing multiple types of cleaning solutions, which permits the selection of a specific solution tailored to the type of contaminants present within the tank 100. This feature ensures that the cleaning process is both effective and efficient. The process includes measures for safe handling and environmental protection, such as ensuring that all chemicals are mixed in a controlled manner and any waste is properly managed.

Step 240 (Maintain adequate pressure during dispensing of the solution): as shown in FIG. 2, at step 240, maintaining adequate pressure during dispensing of the solution using an external water pump 106 connected to the sprinkler nozzles 102, 104. As delineated in FIG. 2, step 240 focuses on the mechanism by which the self-cleaning sectional panel tank 100 maintains the necessary pressure during the dispensing of the cleaning and disinfectant solution. This is achieved by utilizing an external water pump 106 that is operatively connected to the directional sprinkler nozzles 102, 104. The external water pump 106 is pivotal in ensuring that the cleaning and disinfectant solution is propelled through the sprinkler nozzles 102, 104 with adequate force to reach all interior surfaces 1301, 1302, 1303, 1304, 1305 of the tank 100. This pump may be a standard or a booster pump 106, chosen based on the required pressure and flow rate to achieve effective dispersion of the solution.

The water pump 106 is directly connected to the sprinkler nozzles 102, 104. This direct connection is critical to maintain a steady and consistent pressure during the discharge of the cleaning solution, which is essential for the nozzles 102, 104 to operate as intended. The tank 100 includes provisions for regulating the pressure of the solution. This may involve variable speed control on the water pump 106 or other pressure-regulating mechanisms to adjust the pressure according to the size of the tank 100 and the configuration of the sprinkler nozzles 102, 104. The self-cleaning a sectional panel tank 100 may increase water pressure using the booster pump 106 prior to discharging the cleaning solution to enhance the effectiveness of the sprinkler nozzles 102, 104. Maintaining adequate pressure is an integral part of the tank's 100 self-cleaning cycle, ensuring that the cleaning and disinfectant solution is sprayed effectively over the tank's 100 interior surfaces 1301, 1302, 1303, 1304, 1305. The tank 100 includes safety features such as check valves 110, 114, 118 to prevent backflow and automated shut-off mechanisms in case of a malfunction. These features ensure that the tank 100 operates safely and efficiently, avoiding waste of the cleaning solution and potential safety hazards.

Step 250 (Discharge the cleaning and disinfectant solution over interior surfaces): as shown in FIG. 2, at step 250, discharging a cleaning and disinfectant solution over interior surfaces 1301, 1302, 1303, 1304, 1305 of the tank 100 using one or more directional sprinkler nozzles 102, 104. The step 250 encompasses the operational phase of the self-cleaning sectional panel tank 100, where a cleaning and disinfectant solution is dispensed over the tank's 100 interior surfaces 1301, 1302, 1303, 1304, 1305. This process involves the use of one or more directional sprinkler nozzles 102, 104, which are strategically connected to the tank's 100 side walls 1081, 1082, 1083, 1084, 1085, 1086. The directional sprinkler nozzles 102, 104 are activated to discharge a specifically formulated cleaning and disinfectant solution using the conduits 112. These nozzles 102, 104 are designed to ensure that the solution is evenly spread over the entire interior surface of the tank 100, including the ceiling and top edges of the walls.

The discharged solution covers the interior surfaces 1301, 1302, 1303, 1304, 1305 and is left to act for a designated period, ensuring thorough cleaning and disinfection. The tank 100 may include options for the nozzles 102, 104 to either emit a mist or rotate to fill the interior with an aerosolized solution, optimizing the distribution and effectiveness of the cleaning process. The cleaning and disinfectant solution is mixed on-site immediately before each cleaning cycle. This is to prevent the potential hazards of long-term chemical storage and to ensure the potency and efficacy of the solution. The process may be automated using the mixing station equipped with dosing pumps 116, 120 and actuated valves, all managed via Internet of Things (IOT) automation. This technology allows for precise control and monitoring of the cleaning process.

Step 260 (Drain the solution after and cleaning clean interior surfaces 1301, 1302, 1303, 1304, 1305 with clean water or a neutralization chemical after dispensing the solution): as shown in FIG. 2, at step 260, draining the solution after cleaning and cleaning interior surfaces 1301, 1302, 1303, 1304, 1305 with clean water or a neutralization chemical after dispensing the solution. As delineated in FIG. 2, step 260 of the invention's process entails the evacuation of the cleaning and disinfectant solution post-cleaning, followed by a rinse of the interior surfaces 1301, 1302, 1303, 1304, 1305 with clean water or a neutralization chemical. This step is crucial for preparing the tank 100 for its intended use. After the cleaning solution has been allowed to act, the tank 100 may initiate a drainage process. This involves opening drain valves or activating pumps designed to remove the cleaning solution from the tank 100 efficiently. Subsequent to the drainage, the interior surfaces 1301, 1302, 1303, 1304, 1305 of the tank 100 are thoroughly rinsed. This can be done with potable water to remove any residual cleaning agent or with a neutralization chemical if the cleaning solution requires neutralization to prevent any potential harm from leftover residues. The tank 100 may include an integrated system that facilitates both the drainage of the cleaning solution and the subsequent rinse, ensuring that the process is seamless and does not require manual intervention between steps.

The step 260 may be automated, controlled via the Internet of Things automation, which would manage the timing, duration, and sequence of the drainage and rinsing cycles to optimize cleaning effectiveness and water usage. Post-rinse, the tank 100 may typically be left to dry or is filled for use. The self-cleaning sectional panel tank 100 ensures that no harmful levels of cleaning agents remain, maintaining the safety of the potable water. In accordance with an additional or alternative embodiment of the present invention, the self-cleaning a sectional panel tank 100 may inspect the interior surfaces 1301, 1302, 1303, 1304, 1305 of the tank 100 with a camera system after the cleaning process to ensure thorough cleaning and absence of residual contaminants. In accordance with an additional or alternative embodiment of the present invention, the self-cleaning a sectional panel tank 100 may engage an emergency shutdown mechanism via the IoTA upon detection of any malfunction within the sprinkler nozzles 102, 104, dosing pumps 116, 120, or supply lines 124, 126, 128.

Further, in accordance with an additional or alternative embodiment, as shown in FIG. 2, after the completion of the initial cleaning phase where the interior surfaces 1301, 1302, 1303, 1304, 1305 of the tank 100 have been exposed to a cleaning and/or disinfectant solution and then presumably rinsed. A new batch of cleaning and/or disinfectant solution is prepared on-site. The implication is that this is not merely a reuse of the previously mixed solution but rather the preparation of a completely new mixture.

The significance of mixing the solution on-site suggests that the cleaning agents are created in proximity to the tank 100, ensuring freshness and potency of the solution while also potentially allowing for customization based on the immediate cleaning needs observed after the first cycle. This could be especially important if the initial cleaning cycle indicated areas that require a stronger or differently formulated solution. For instance, if the first cycle was primarily disinfectant, the second might focus on removing mineral deposits or vice versa.

The present invention offers several technical advantages over the existing prior arts, significantly improving the process of maintaining sectional panel tanks:

The invention automates the cleaning process, removing the variability and inconsistency of manual cleaning. Automated systems can achieve a high degree of precision and consistency, ensuring that the entire interior surface of the tank is subjected to a thorough cleaning cycle. By eliminating the need for manual entry into the tanks for cleaning purposes, the invention significantly reduces labour costs and enhances worker safety. There is less risk of exposure to hazardous environments and substances, and the need for confined space entry permits is diminished. The self-cleaning process can be executed with the tank in-situ and possibly even in operation, which minimizes downtime. This is particularly beneficial in industrial applications where tank availability is critical to ongoing processes.

The invention's design allows for the directional sprinkler nozzles to reach all interior areas of the tank, including corners and other hard-to-clean areas, which might be overlooked or inaccessible during manual cleaning. Efficient Use of Cleaning Agents: The system is designed to precisely mix and meter the cleaning and disinfectant solutions, reducing waste and ensuring that the correct concentration of cleaning agents is used. This not only conserves chemicals but also minimizes the environmental impact of the cleaning process. With the capability of more frequent and reliable cleaning cycles, the invention helps maintain a high level of hygiene within the tank. This is crucial for tanks used in potable water systems, food and beverage industries, and any application where water quality is paramount. The automated and consistent cleaning process facilitates compliance with stringent health and safety regulations. With integrated sensors and IoT connectivity, the tank 100 can provide real-time data and records of cleaning cycles, aiding in regulatory reporting and compliance.

The reduction in manual labour, improved cleaning efficiency, and minimized chemical usage result in a cost-effective solution over the long term. The tank's 100 reliability and efficiency also reduce the potential costs associated with contamination or regulatory non-compliance. The inclusion of Internet of Things (IOT) technologies allows for advanced monitoring and control of the cleaning process. This can lead to predictive maintenance schedules, remote diagnostics, and immediate alerts if issues are detected, further enhancing the tank's 100 reliability and performance. The design of the invention allows for integration into existing tank infrastructures with minimal modifications, making it a flexible solution that can be adapted to a wide range of tank sizes and configurations.

The technical advantages of the present invention create a more efficient, safe, and compliant environment for the storage and maintenance of liquids in sectional panel tanks, offering substantial improvements over the methods and systems found in prior art.

In the application, unless specified otherwise, the terms "comprising", "comprise", and grammatical variants thereof, intended to represent "open" or "inclusive" language such that they include recited elements but also permit inclusion of additional, non-explicitly recited elements.

Various modifications to these embodiments are apparent to those skilled in the art from the description and the accompanying drawings. The principles associated with the various embodiments described herein may be applied to other embodiments. Therefore, the description is not intended to be limited to the embodiments shown along with the accompanying drawings but is to be providing broadest scope consistent with the principles and the novel and inventive features disclosed or suggested herein. Accordingly, the application is anticipated to hold on to all other such alternatives, modifications, and variations that fall within the scope of the present application and the appended claims.

REFERENCE NUMERALS

100—A self-cleaning sectional panel tank/The self-cleaning sectional panel tank/This self-cleaning sectional panel tank/the tank.
102—Fixed nozzles/sprinkler nozzles/the nozzles/these nozzles
104—Rotatable nozzles/the nozzles/sprinkler nozzles/these nozzles
106—External water pump or booster pump/pump/external pump/water pump
1081—First side wall/side wall/wall
1082—Second side wall/side wall
1083—Third side wall/side wall
1084—Fourth side wall/side wall
1085—Fifth side wall/side wall
1086—Sixth side wall/side wall
1091—First unit panel/unit panel/multiple unit panels/the panels/two-unit panels
1092—Second unit panel/unit panel/multiple unit panels/the panels/two-unit panels
110—Third check valve/check valves/
112—Motorized valve
114—Second check valve/check valves
116—Second dosing pump/dosing pumps/pump
118—First check valve/check valves
120—First dosing pump/dosing pumps/pump
122—Conduit/Multiple Conduits
124—First supply line/supply lines
126—Second supply line/supply lines
128—Third supply line/supply lines
1301—First interior surface/interior surfaces
1302—Second interior surface/interior surfaces
1303—Third interior surface/interior surfaces
1304—Forth interior surface/interior surfaces
1305—Fifth interior surface/interior surfaces
200—A Method of Working of The Self-Cleaning Sectional Panel Tank
210—Provide At Least One Side Wall 220—Join the First Unit Panel and The Second Unit Panel
230—Mix A Cleaning and/or Disinfectant Solution On-Site
240—Maintain Adequate Pressure During Dispensing of The Solution
250—Discharge the Cleaning and Disinfectant Solution Over Interior Surfaces
260—Drain the Solution After and Cleaning Clean Interior Surfaces with Clean Water or A Neutralization Chemical After Dispensing the Solution

The invention claimed is:

1. A self-cleaning sectional panel tank, comprising:
at least one side wall for joining other side walls in forming the sectional panel tank;
wherein the at least one side wall comprises:
a first unit panel having a first extension at its edge for supporting the first unit panel; and
a second unit panel having a second extension at its edge;
wherein the first unit panel and the second unit panel are joined together contiguously at the first extension and the second extension by at least one fastener; and
at least one directional sprinkler nozzle connected to the at least one side wall configured to discharge a cleaning and/or disinfectant solution onto interior surfaces of the self-cleaning sectional panel tank.

2. The self-cleaning sectional panel tank of claim 1, further comprising an external water pump connected to the at least one directional sprinkler nozzle using at least one conduit for maintaining pressure in order to dispense of the cleaning and/or disinfectant solution.

3. The self-cleaning sectional panel tank of claim 2, wherein the external water pump is a booster pump configured to increase pressure of the water for the sprinkler nozzle to ensure reach and dispersion of the cleaning and/or disinfectant solution.

4. The self-cleaning sectional panel tank of claim 2, further comprising:
inline sensors integrated within supply lines connected with the external water pump for monitoring water quality after cleaning to detect any residual solution or deterioration in water quality.

5. The self-cleaning sectional panel tank of claim 4, further comprising check valves integrated into the supply lines to prevent backflow and ensure the directional flow of the cleaning and/or disinfectant solution.

6. The self-cleaning sectional panel tank of claim 4, further comprising motorized valves in the supply lines controlled by IoTA for automated regulation of a flow of potable water and cleaning chemicals into the mixing station.

7. The self-cleaning sectional panel tank of claim 1, wherein the interior surfaces are cleaned with water or a neutralization chemical after dispensing the cleaning and/or disinfectant solution.

8. The self-cleaning sectional panel tank of claim 1, wherein the at least one directional sprinkler nozzle comprises multiple directional sprinkler nozzles, and wherein the at least one or multiple directional sprinkler nozzles are configured to rotate to aerosolize the solution within the interior of the tank.

9. The self-cleaning sectional panel tank of claim 1, wherein the at least one directional sprinkler nozzle includes fixed and rotatable sprinkler heads, the fixed heads for a uniform stream and the rotatable heads for covering variable angles within the interior of the tank.

10. The self-cleaning sectional panel tank of claim 1, further comprising a mixing station configured to automate dispense the cleaning and/or disinfectant solution and/or uncontaminated water using a series of dosing pumps and actuated valves using Internet of Things automation (IoTA).

11. The self-cleaning sectional panel tank of claim 10, wherein the mixing station is configured to prepare multiple types of cleaning solutions, allowing for selection of a specific solution based on the contaminants present in the tank.

12. A method for a self-cleaning a sectional panel tank, comprising:

providing at least one side wall, wherein the at least one side wall comprises a first unit panel with a first extension at its edge and a second unit panel with a second extension at its edge;

joining the first unit panel and the second unit panel together contiguously at the first extension and the second extension using at least one fastener;

mixing a cleaning and/or disinfectant solution on-site before initiating any cleaning process;

discharging the cleaning and disinfectant solution over interior surfaces of the tank using one or more directional sprinkler nozzles;

maintaining pressure during dispensing of the cleaning and/or disinfectant solution using an external water pump connected to the directional sprinkler nozzles;

draining the solution after cleaning; and cleaning interior surfaces with uncontaminated water or a neutralization chemical after dispensing the solution.

13. The method of claim 12, comprising a step of rotating the directional nozzles to aerosolize the solution, thereby covering a comprehensive area within the interior of the tank.

14. The method of claim 12, further comprising a step of automating the dispensing of the cleaning and/or disinfectant solution and/or uncontaminated water using a mixing station configured with a series of dosing pumps and actuated valves utilizing Internet of Things automation (IoTA).

15. The method for self-cleaning a sectional panel tank as in claim 14, further including step of metering and introducing multiple cleaning chemicals into the mixing station using a plurality of dosing pumps, where individual pumps are connected to a separate supply line for different chemicals.

16. The method for self-cleaning a sectional panel tank as in claim 14, further comprising the step of automating flow regulation of potable water and chemicals into the mixing station via motorized valves controlled by Internet of Things automation (IoTA).

17. The method of claim 12, further comprising steps of:

integrating inline sensors within supply lines connected with the external pump to monitor water quality after cleaning to detect any residual solution or deterioration in water quality; and utilizing IoTA to inform relevant authorities of fulfilment of statutory requirements for maintaining potable water tanks.

18. The method for self-cleaning a sectional panel tank as in claim 12, further comprising the steps of activating fixed and rotatable sprinkler heads, wherein the fixed heads provide a continuous stream and the rotatable heads cover variable angles to ensure complete coverage of the tank interior.

19. The method for self-cleaning a sectional panel tank as in claim 12, further including the step of increasing water pressure using a booster pump prior to discharging the cleaning solution to enhance effectiveness of the sprinkler nozzles.

20. The method for self-cleaning a sectional panel tank as in claim 12, wherein after cleaning the interior surfaces, mixing another cleaning and/or disinfectant solution on-site.

\* \* \* \* \*